(12) United States Patent
Katsurahara et al.

(10) Patent No.: US 9,052,280 B2
(45) Date of Patent: *Jun. 9, 2015

(54) DETERIORATION DIAGNOSIS DEVICE FOR CATALYST

(71) Applicant: DENSO CORPORATION, Kariya, Aichi-pref. (JP)

(72) Inventors: Hiroshi Katsurahara, Okazaki (JP); Shingo Nakata, Kariya (JP); Mikiyasu Matsuoka, Obu (JP)

(73) Assignee: DENSO CORPORATION, Kariya (JP)

( * ) Notice: Subject to any disclaimer, the term of this patent is extended or adjusted under 35 U.S.C. 154(b) by 135 days.

This patent is subject to a terminal disclaimer.

(21) Appl. No.: 13/761,542

(22) Filed: Feb. 7, 2013

(65) Prior Publication Data

US 2013/0206596 A1    Aug. 15, 2013

(30) Foreign Application Priority Data

Feb. 10, 2012    (JP) .................................. 2012-026906

(51) Int. Cl.
  *G01N 27/407*    (2006.01)

(52) U.S. Cl.
  CPC ..................................... *G01N 27/407* (2013.01)

(58) Field of Classification Search
  CPC . G01M 15/10; G01M 15/102; G01M 15/104; G01N 1/2252; G01N 27/404–27/407; G01N 27/409; G01N 27/419
  USPC ........................ 204/421–429; 73/23.31, 23.32
  See application file for complete search history.

(56) References Cited

U.S. PATENT DOCUMENTS

| | | | |
|---|---|---|---|
| 4,741,817 A | 5/1988 | Croset et al. | |
| 5,383,333 A | 1/1995 | Logothetis et al. | |
| 6,370,935 B1 | 4/2002 | He et al. | |
| 2003/0196428 A1* | 10/2003 | Iida et al. | 60/285 |
| 2008/0092524 A1* | 4/2008 | Yokoyama et al. | 60/277 |

(Continued)

FOREIGN PATENT DOCUMENTS

| | | |
|---|---|---|
| JP | 61-118653 | 6/1986 |
| JP | 03-258947 | 11/1991 |
| JP | 2011-196317 | 10/2011 |

OTHER PUBLICATIONS

Office Action (2 pages) dated Oct. 30, 2014, issued in corresponding Japanese Application No. 2012-026906 and English translation (3 pages).

*Primary Examiner* — Jennifer Dieterle (74) *Attorney, Agent, or Firm* — Nixon & Vanderhye P.C.

(57) ABSTRACT

A deterioration diagnosis device, which performs a deterioration diagnosis of a catalyst, includes an exhaust-gas sensor provided downstream of the catalyst in a flow direction of exhaust gas such that an output value of the exhaust-gas sensor is used at least in the deterioration diagnosis. The deterioration diagnosis device further includes the constant current supply portion which applies a voltage to a sensor element of the exhaust-gas sensor to change an output characteristic of the exhaust-gas sensor, a response-time detection portion which detects a response time required for the output value of the exhaust-gas sensor to change from a rich threshold to a lean threshold, a response-time correction portion which controls the constant current supply portion to change the output characteristic of the exhaust-gas sensor so as to shorten the response time when the response time is longer than a predetermined reference time.

9 Claims, 9 Drawing Sheets

(56) References Cited

U.S. PATENT DOCUMENTS

| | | |
|---|---|---|
| 2009/0145110 A1 | 6/2009 | Fukuchi et al. |
| 2010/0050602 A1* | 3/2010 | Fujimoto ........................ 60/277 |
| 2010/0199638 A1* | 8/2010 | Yoshikawa ..................... 60/277 |
| 2011/0192146 A1* | 8/2011 | Sugimoto et al. ............... 60/276 |
| 2012/0034569 A1* | 2/2012 | Sakamoto et al. .............. 431/76 |
| 2012/0043205 A1* | 2/2012 | Matsuoka et al. ............. 204/410 |
| 2013/0019653 A1* | 1/2013 | Nakata ........................ 73/23.33 |

* cited by examiner

FIG. 8    COMPARATIVE EXAMPLE

FIG. 12

DETERIORATION DIAGNOSIS DEVICE FOR CATALYST

CROSS REFERENCE TO RELATED APPLICATION

This application is based on and incorporates herein by reference Japanese Patent Application No. 2012-026906 filed on Feb. 10, 2012.

TECHNICAL FIELD

The present disclosure relates to a deterioration diagnosis device which performs a deterioration diagnosis of a catalyst by using an output of a downstream exhaust-gas sensor provided downstream of the catalyst that is used for purification of exhaust gas discharged from an internal combustion engine.

BACKGROUND

Conventionally, for purpose of improvement of catalytic conversion efficiency of a catalyst used for purification of exhaust gas, an emission control system for an internal combustion engine includes exhaust-gas sensors (e.g., an air/fuel sensor and an oxygen sensor) that are respectively disposed upstream and downstream of the catalyst in a flow direction of the exhaust gas. The exhaust-gas sensors detect an air-fuel ratio of the exhaust gas or detect whether the exhaust gas is rich or lean, and the emission control system controls the air-fuel ratio by a feedback control based on the outputs of the exhaust-gas sensors.

When the air-fuel ratio of the exhaust gas changes from rich to lean or from lean to rich, an output change of the exhaust-gas sensor (e.g., an oxygen sensor) may lag behind a change of an actual air-fuel ratio of the exhaust gas. Thus, the exhaust-gas sensor may have a room for improvement in detection responsiveness.

For example, as described in Patent Document 1 (JP 8-20414 corresponding to U.S. Pat. No. 4,741,817), at least one of an auxiliary electrochemical cell is incorporated to an inside of a gas sensor such as an oxygen sensor for increase in detection responsiveness.

A deterioration diagnosis technology for a catalyst is known. In the diagnosis technology, for example, a rich combustion control and a lean combustion control are performed alternately. In the rich combustion control, an air-fuel ratio of air/fuel mixture supplied to an engine is controlled to become richer. In the lean combustion control, the air-fuel ratio of the air/fuel mixture supplied to the engine is controlled to become leaner. During a predetermined period of the alternately-performed rich and lean combustion controls, a calculation portion calculates a ratio between an integrated value of output values of a downstream exhaust-gas sensor located downstream of the catalyst and an integrated value of output values of an upstream oxygen sensor located upstream of the catalyst. Subsequently, the integrated value ratio is compared with a predetermined reference value. Accordingly, a deterioration diagnosis of the catalyst is performed, in other words, for example, it is determined whether an oxygen storage capacity of the catalyst is small.

When a detection responsiveness of the downstream exhaust-gas sensor decreases due to time deterioration for example, output behaviors of the downstream exhaust-gas sensor may be similar between when the catalyst is deteriorated and when the catalyst is normal (i.e., not deteriorated) in the deterioration diagnosis. Thus, even when the catalyst is deteriorated, it may be determined that the catalyst is normal (i.e., not deteriorated). Therefore, a reference value for determining the decrease of the detection responsiveness of the downstream exhaust-gas sensor may be necessarily set tightly, and a life time of the downstream exhaust-gas sensor may thereby become short. In other words, the time to exchange the downstream exhaust-gas sensor due to the decrease of its detection responsiveness may become earlier.

In Patent Document 1, the auxiliary electrochemical cell is necessarily incorporated into the inside of the gas sensor. Thus, when the auxiliary electrochemical cell is incorporated into a general gas sensor that does not have an auxiliary electrochemical cell, the general gas sensor may need to be changed greatly in structure. For practical use, the gas sensor may be required to be changed in design, and a manufacturing cost of the gas sensor may be increased.

It is an objective of the present disclosure to provide a deterioration diagnosis device for a catalyst, which is capable of changing an output characteristic of a downstream exhaust-gas sensor without great change in design and cost increase, and capable of limiting a decrease of an accuracy of a deterioration diagnosis due to a decrease of a detection responsiveness of the downstream exhaust-gas sensor.

SUMMARY

According to an aspect of the present disclosure, a deterioration diagnosis device performs a deterioration diagnosis of a catalyst used for purification of exhaust gas discharged from an internal combustion engine. The deterioration diagnosis device includes a downstream exhaust-gas sensor, a constant current supply portion, a response-time detection portion and a response-time correction portion. The downstream exhaust-gas sensor is provided downstream of the catalyst in a flow direction of the exhaust gas to detect and output an air-fuel ratio of the exhaust gas or to detect and output whether the exhaust gas is rich or lean such that an output value of the downstream exhaust-gas sensor is used in at least in the deterioration diagnosis. The downstream exhaust-gas sensor includes a sensor element that includes a pair of electrodes and a solid electrolyte body located between the pair of electrodes. The constant current supply portion applies a constant current and a voltage to the pair of electrodes to change an output characteristic of the downstream exhaust-gas sensor. The response-time detection portion detects a response time required for the output value of the downstream exhaust-gas sensor to change from a predetermined rich threshold to a predetermined lean threshold during a fuel-cut control in which fuel injection of the engine is stopped. The response-time correction portion changes the output characteristic of the downstream exhaust-gas sensor by controlling the constant current supply portion and applying the constant current and the voltage to the pair of electrodes so as to shorten the response time when the response time detected by the response-time detection portion is longer than a predetermined reference time.

Accordingly, the output characteristic of the exhaust-gas sensor can be changed by applying the constant current between the pair of electrodes. In this case, there is no need to incorporate an auxiliary electrochemical cell or the like to an inside of the exhaust-gas sensor. Therefore, the output characteristic of the exhaust-gas sensor can be changed without great design changes and cost increase.

When the response time detected during the fuel-cut control of the engine is determined to be longer than the reference time, the constant current supply portion is controlled to apply the sensor voltage to the sensor electrodes of the downstream exhaust-gas sensor so that a constant current flows between the sensor electrodes. Accordingly, the output characteristic of the downstream exhaust-gas sensor is changed so that the response time is shortened. Therefore, when a detection responsiveness of the downstream exhaust-gas sensor is low, the output characteristic of the downstream exhaust-gas sensor can be changed such that the detection responsiveness of the downstream exhaust-gas sensor is increased. As a result, it can be avoided that an output behavior of the downstream exhaust-gas sensor becomes similar between when the catalyst is not deteriorated and when the catalyst is deteriorated. Therefore, when the catalyst is deteriorated, it can be restricted that the catalyst is determined not to be deteriorated, i.e., it can be restricted that the catalyst is determined to be normal. In other words, the catalyst can be determined to be deteriorated accurately when the catalyst is deteriorated. Consequently, decrease of an accuracy of the deterioration diagnosis of the catalyst due to the decrease of the detection responsiveness of the downstream exhaust-gas sensor can be restricted. The accuracy of the deterioration diagnosis of the catalyst can be increased. Furthermore, there can be no need to set so tightly a reference value that is for determining the decrease of the detection responsiveness of the downstream exhaust-gas sensor, and the life time of the downstream exhaust-gas sensor can be thereby lengthened. In other words, the time to exchange the downstream exhaust-gas sensor due to decrease of its detection responsiveness can be retarded.

The deterioration diagnosis device may further include a diagnosis control portion which inhibits the deterioration diagnosis of the catalyst when the response time is longer than the reference time, and enables the deterioration diagnosis to be performed when the response time is equal to or shorter than the reference time. In this case, when the response time is equal to or shorter than the reference time, correction of the detection responsiveness of the downstream exhaust-gas sensor can be determined to be finished, and the deterioration diagnosis of the catalyst can be enabled to be performed.

BRIEF DESCRIPTION OF THE DRAWINGS

The disclosure, together with additional objectives, features and advantages thereof, will be best understood from the following description, the appended claims and the accompanying drawings, in which:

DETAILED DESCRIPTION

An exemplar embodiment of the present disclosure will be described with reference to FIGS. 1 to 9. First, an emission control system 1 of the present embodiment will be described based on FIG. 1. The emission control system 1 can be used as an example of a deterioration diagnosis device of the present disclosure. The emission control system 1 includes an engine 11 (internal combustion engine), an intake pipe 12 through which intake air flows to be drawn into the engine 11, a throttle valve 13 provided in the intake pipe 12, and a throttle sensor 14 provided in the intake pipe 12. An open degree (throttle-open degree) of the throttle valve 13 is adjusted by using a motor or the like, and the throttle sensor 14 detects the throttle-open degree of the throttle valve 13. The engine 11 includes fuel injection valves 15 attached respectively to cylinders of the engine 11 to inject fuel into the cylinders or into intake ports of the cylinders, and spark plugs 16 provided in a cylinder head of the engine 11 adjacent to the cylinders respectively. The spark plugs 16 generate electric spark to ignite air/fuel mixture in the cylinders.

Figure 1:
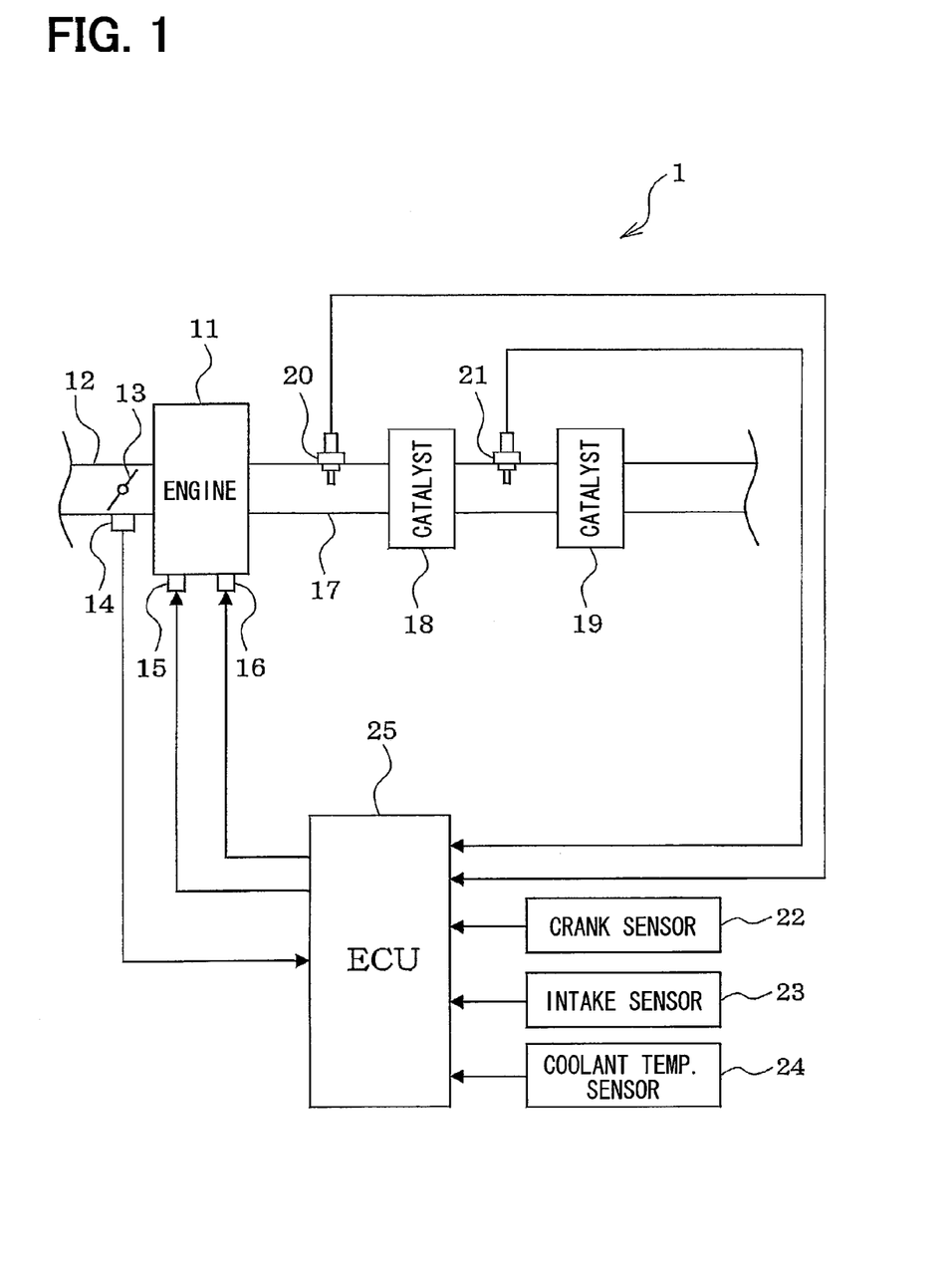
FIG. 1 is a schematic diagram showing an emission control system that can be used as a deterioration diagnosis device according to an exemplar embodiment of the present disclosure.

The emission control system 1 further includes an exhaust pipe 17 through which exhaust gas discharged from the engine 11 passes, an upstream catalyst 18 (purification catalyst) provided in the exhaust pipe 17, a downstream catalyst 19 arranged downstream of the upstream catalyst 18 in a flow direction of the exhaust gas in the exhaust pipe 17, an upstream oxygen sensor 20 (upstream sensor) arranged upstream of the upstream catalyst 18 in the exhaust-gas flow direction in the exhaust pipe 17, and a downstream oxygen sensor 21 (downstream exhaust-gas sensor, downstream sensor) arranged downstream of the upstream catalyst 18, i.e., between the upstream catalyst 18 and the downstream catalyst 19 in the exhaust-gas flow direction in the exhaust pipe 17. The upstream catalyst 18 and the downstream catalyst 19 are, for example, three-way catalysts that purify substances, such as carbon monoxide (CO), hydrocarbon (HC) and nitrogen oxide (NOx), contained in the exhaust gas. The upstream oxygen sensor 20 and the downstream oxygen sensor 21 respectively detect whether the exhaust gas is rich or lean. When the air-fuel ratio is higher than the stoichiometric air-fuel ratio, it can be said that the air-fuel ratio is lean. When the air-fuel ratio is lower than the stoichiometric air-fuel ratio, it can be said that the air-fuel ratio is rich.

Additionally, the emission control system 1 includes various sensors that includes a crank sensor 22 that outputs a pulse signal at each predetermined rotation angle (i.e., crank angle) of a crankshaft of the engine 11, an intake sensor 23 that detects an intake air amount drawn into the engine 11, and a coolant temperature sensor 24 that detects a temperature of coolant for the engine 11. The rotation angle of the crankshaft and a rotation speed of the engine 11 are determined based on the signal outputted from the crank sensor 22.

Outputs of the above-described various sensors are input to an electronic control unit (ECU) 25. The ECU 25 includes a microcomputer 26 shown in FIG. 2, and executes a variety of engine control programs stored in a read-only memory (ROM) embedded in the microcomputer, so that the ECU 25 controls, for example, a fuel-injection amount, an ignition timing and the throttle degree (intake air amount) based on an operational state of the engine 11.

Next, the downstream oxygen sensor 21 will be described based on FIG. 2. The downstream oxygen sensor 21 includes a sensor element 31 having a cup-like shape. The sensor element 31 is accommodated in a housing or an element case, and is arranged in the exhaust pipe 17 connected to the engine 11.

Figure 2:
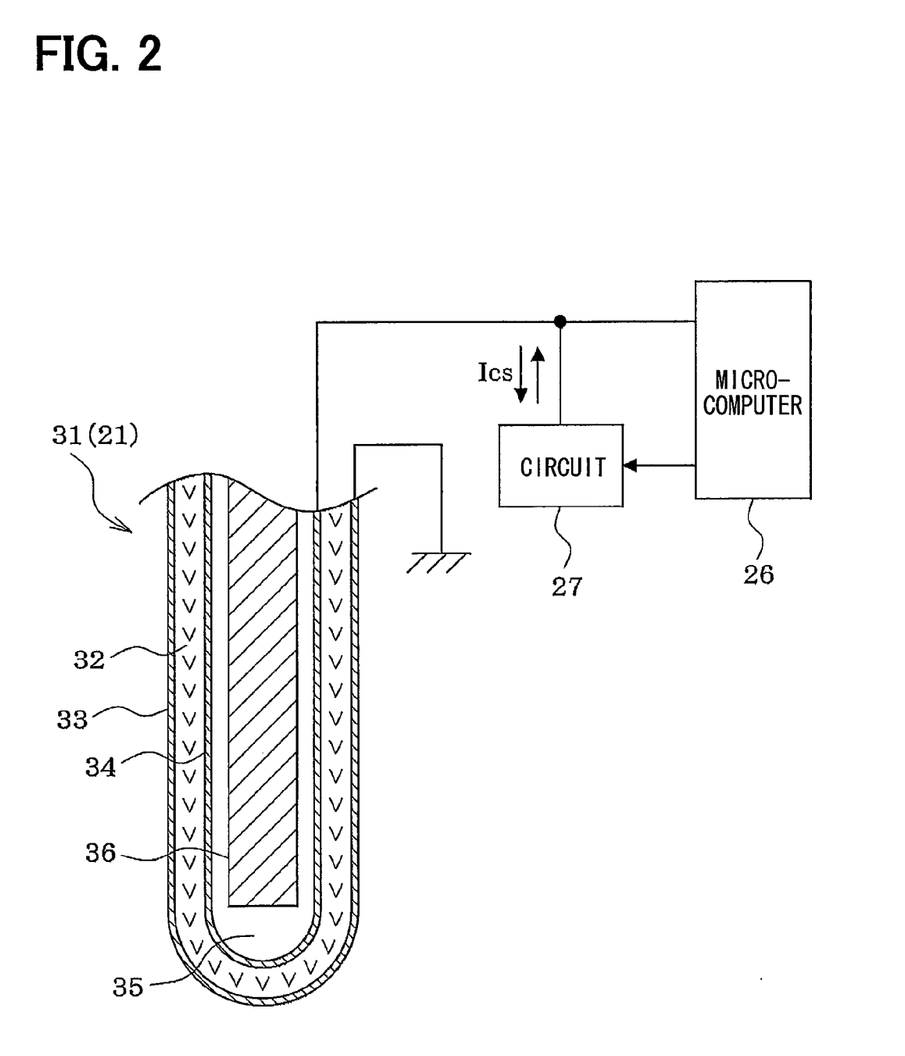
FIG. 2 is a schematic diagram showing a sectional view of a sensor element, a constant current circuit and a microcomputer of the emission control system according to the exemplar embodiment.

The sensor element 31 has a cup-like shape in sectional surface as shown in FIG. 2. The sensor element 31 includes a solid electrolyte layer 32 (solid electrolyte body), an exhaust electrode layer 33 provided on an outer periphery of the solid electrolyte layer 32, and an atmosphere electrode layer 34 provided on an inner periphery of the solid electrolyte layer 32. The solid electrolyte layer 32 is made, for example, of an oxide sintered body having an oxygen-ion conductivity. The oxide sintered body is a solid solution in which a solute, such as CaO, MgO, $Y_2O_3$ or $Yb_2O_3$, is dissolved as a stabilizing agent in a solvent, such as $ZrO_2$, $HfO_2$, $ThO_2$ or $Bi_2O_3$. The electrode layers 33 and 34 are made of noble metal superior in catalytic activity, such as platinum, and are covered with a porous material via chemical plating treatment. These electrode layers 33 and 34 are used as an example of a pair of electrodes (sensor electrodes) which are opposed to each other. The sensor element 31 further includes an atmosphere space 35 surrounded by the atmosphere electrode layer 34, and a heater 36 accommodated in the atmosphere space 35. The heater 36 has a heating capacity enough to activate the sensor element 31, and the sensor element 31 is thereby heated as a whole by heat energy generated by the heater 36. An activation temperature of the downstream oxygen sensor 21 is, for example, approximately from 350° C. to 400° C. The atmosphere space 35 introduces air therein from atmosphere so that an oxygen concentration in the atmosphere space 35 is kept at a predetermined degree.

The exhaust gas flows on outer side of the solid electrolyte layer 32 of the sensor element 31, in other words, the exhaust electrode layer 33 is exposed to the exhaust gas. The air introduced from atmosphere into the sensor element 31 is trapped on an inner side of the solid electrolyte layer 32, in other words, the atmosphere electrode layer 34 is exposed to the introduced air. Hence, an electromotive force is generated between the electrode layers 33 and 34 depending on a difference of an oxygen concentration (oxygen partial pressure) between in the exhaust gas and in the introduced air. Hence, the sensor element 31 generates an electromotive force that changes depending on whether the air-fuel ratio of the exhaust gas is rich or lean. Accordingly, the downstream oxygen sensor 21 outputs a signal of the electromotive force dependent on the oxygen concentration (i.e., air-fuel ratio) of the exhaust gas.

Figure 3:
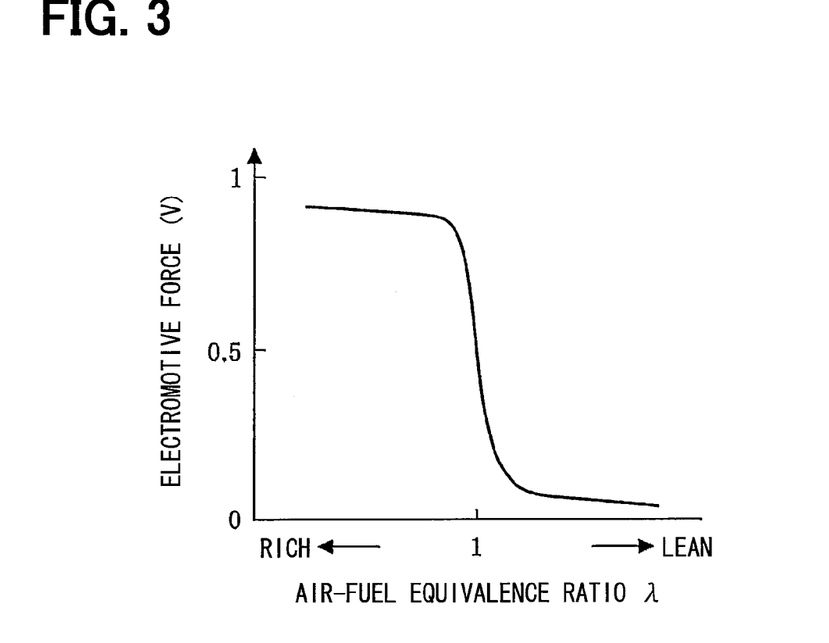
FIG. 3 is a diagram showing a relationship between an air-fuel ratio (air-fuel equivalence ratio X) of exhaust gas and an electromotive force generated by the sensor element according to the exemplar embodiment.

As shown in FIG. 3, the sensor element 31 generates an electromotive force that changes depending whether the air-fuel ratio of the exhaust gas is larger or smaller than the stoichiometric air-fuel ratio, i.e., whether the air-fuel ratio of the exhaust gas is lean or rich. In FIG. 3, when the air-fuel ratio of the exhaust gas is equal to the stoichiometric air-fuel ratio, an air-fuel equivalence ratio $\lambda$ is equal to 1. The sensor element 31 has a characteristic such that the electromotive force generated by the sensor element 31 changes dramatically near the stoichiometric air-fuel ratio at which the air-fuel equivalence ratio $\lambda$ is equal to 1. The sensor element 31 generates a rich electromotive force when the air-fuel ratio is rich, and the sensor element 31 generates a lean electromotive force different from the rich electromotive force in voltage value when the air-fuel ratio is lean. For example, the rich electromotive force is approximately 0.9 V, and the lean electromotive force is approximately 0 V.

As shown in FIG. 2, the exhaust electrode layer 33 of the sensor element 31 is grounded, and the atmosphere electrode layer 34 is connected to the microcomputer 26. When the sensor element 31 generates an electromotive force depending on the air-fuel ratio (i.e., oxygen concentration) of the exhaust gas, a detection signal corresponding to the generated electromotive force is output to the microcomputer 26. The microcomputer 26 is, for example, provided in the ECU 25, and calculates the air-fuel ratio of the exhaust gas based on the detection signal. The microcomputer 26 may calculate a rotational speed of the engine 11 or an intake air amount based on detection results of the above-described various sensors.

When the engine 11 is operating, an actual air-fuel ratio of the exhaust gas may alternate between rich and lean repeatedly. In such case, if the downstream oxygen sensor 21 is low in its detection responsiveness, performance of the engine 11 may be affected. For example, in a high-load operation of the engine 11, an amount of NOx in the exhaust gas may become larger than expected.

Figure 4A:
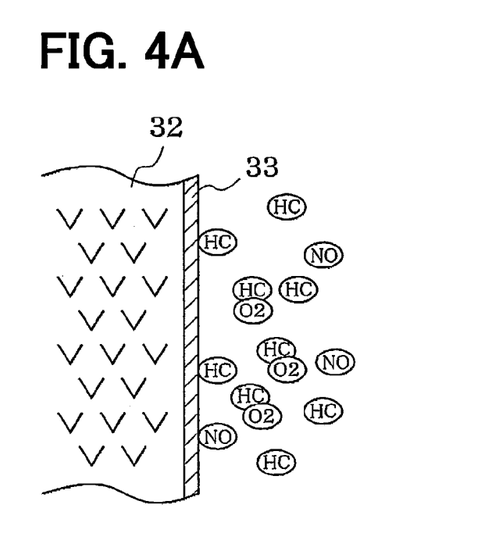
FIG. 4A is a schematic diagram showing a state of components of the exhaust gas around the sensor element when an actual air-fuel ratio changes from rich to lean, according to the exemplar embodiment.
Figure 4B:
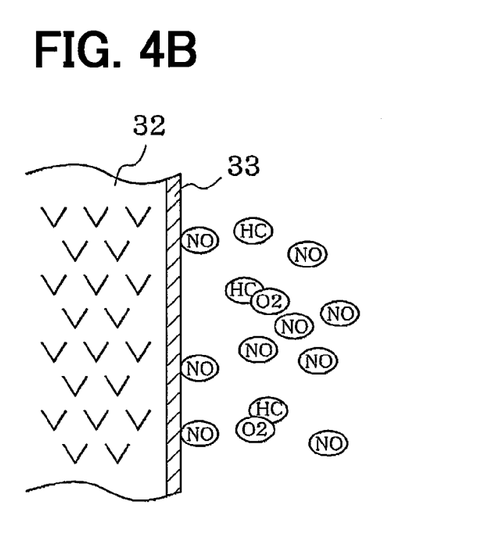
FIG. 4B is a schematic diagram showing a state of components of the exhaust gas around the sensor element when the actual air-fuel ratio changes from lean to rich, according to the exemplar embodiment.

The detection responsiveness of the downstream oxygen sensor 21 in a case where the actual air-fuel ratio of the exhaust gas changes from rich to lean or from lean to rich will be described. When the actual air-fuel ratio of the exhaust gas discharged from the engine 11 (i.e., the actual air-fuel ratio of the exhaust gas flowing downstream of the upstream catalyst 18) changes from rich to lean or from lean to rich, component composition of the exhaust gas changes. Components of exhaust gas, which flows around the downstream oxygen sensor 21 immediately before the change of the actual air-fuel ratio, may remain around the downstream oxygen sensor 21 immediately after the change of the actual air-fuel ratio. Here, the output of the downstream oxygen sensor 21 changes in accordance with the change of the actual air-fuel ratio. Therefore, the remained components around the downstream oxygen sensor 21 may cause the output change of the downstream oxygen sensor 21 to retard. In other words, the detection responsiveness of the downstream oxygen sensor 21 may decrease. Specifically, immediately after the actual air-fuel ratio changes from rich to lean as shown in FIG. 4A, a rich component such as HC remains around the exhaust electrode layer 33, and disturbs a reaction of a lean component such as NOx. As a result, detection responsiveness of the downstream oxygen sensor 21 may decrease when the actual air-fuel ratio changes from rich to lean. Immediately after the actual air-fuel ratio changes from lean to rich as shown in FIG. 4B, the lean component such as NOx remains around the exhaust electrode layer 33, and disturbs a reaction of the rich component such as HC. As a result, the detection responsiveness of the downstream oxygen sensor 21 may decrease also when the actual air-fuel ratio from lean to rich.

Figure 5:
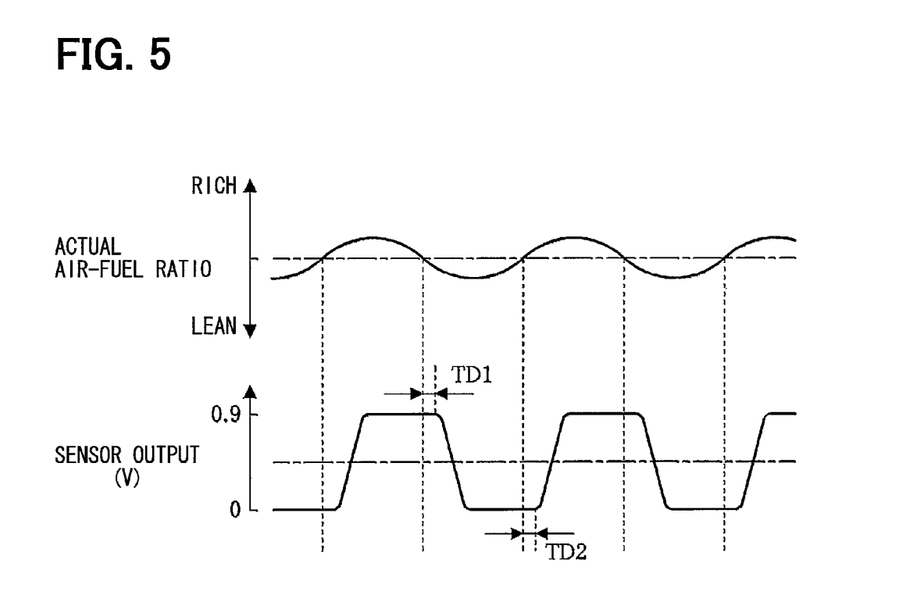
FIG. 5 is a time chart showing behavior of a sensor output in accordance with change of the actual air-fuel ratio in a case where a constant current is not applied to the sensor element, according to the exemplar embodiment.

The output change of the downstream oxygen sensor 21 in a case where a constant current Ics described later is not applied to the sensor element 31 will be described referring to FIG. 5. When the actual air-fuel ratio alternates between rich and lean, an output (sensor output) of the downstream oxygen sensor 21 alternates between the rich electromotive force (e.g., 0.9 V) and the lean electromotive force (e.g., 0 V) in accordance with the alternation of the actual air-fuel ratio. In this case, the change of the sensor output lags behind the change of the actual air-fuel ratio. As shown in FIG. 5, when the actual air-fuel ratio changes from rich to lean, the sensor output of the downstream oxygen sensor 21 changes behind the change of the actual air-fuel ratio by a time TD1. When the actual air-fuel ratio changes from lean to rich, the sensor output of the downstream oxygen sensor 21 changes behind the change of the actual air-fuel ratio by a time TD2.

In the present embodiment, as shown in FIG. 2, a constant current circuit 27 is connected to the atmosphere electrode layer 34. The constant current circuit 27 may be used as an example of a constant current supply portion that supplies a constant current and a voltage between the electrode layers 33 and 34. The microcomputer 26 controls the constant current circuit 27 to supply a constant current Ics to the exhaust electrode layer 33 and the atmosphere electrode layer 34, so that the constant current Ics flows in a predetermined direction between the electrode layers 33, 34. Accordingly, the constant current circuit 27 changes an output characteristic of the downstream oxygen sensor 21 such that the detection responsiveness of the downstream oxygen sensor 21 changes. The microcomputer 26 determines a flow direction and a flow rate of the constant current Ics that is to flow between the electrode layers 33, 34, and the microcomputer 26 controls the constant current circuit 27 so that the constant current Ics flows in the determined flow direction and at the determined flow rate.

Specifically, the constant current circuit 27 supplies the constant current Ics in positive value or negative value to the atmosphere electrode layer 34, and the constant current circuit 27 is capable of adjusting the constant current Ics variably. In other words, the microcomputer 26 variably controls the constant current Ics applied to the sensor electrodes (the exhaust electrode layer 33 and the atmosphere electrode layer 34) by a pulse width modulation control (PMW control). In the constant current circuit 27, the constant current Ics is adjusted depending on a duty-cycle signal output from the microcomputer 26, and the adjusted constant current Ics is supplied to between the sensor electrodes.

In the present embodiment, the constant current Ics flowing from the exhaust electrode layer 33 to the atmosphere electrode layer 34 is defined as a negative constant current (−Ics), and the constant current Ics flowing from the atmosphere electrode layer 34 to the exhaust electrode layer 33 is defined as a positive constant current (+Ics).

Figure 6A:
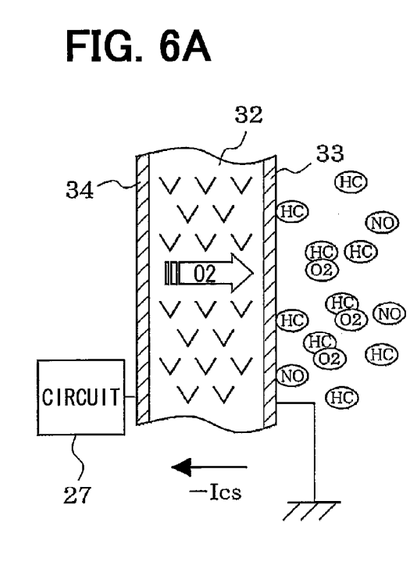
FIG. 6A is a schematic diagram showing a state of components of the exhaust gas around the sensor element when the actual air-fuel ratio changes from rich to lean, and showing a current direction in the sensor element when a lean responsiveness of the sensor element is increased, according to the exemplar embodiment.

When the detection responsiveness of the downstream oxygen sensor 21 is increased in a case where the actual air-fuel ratio changes from rich to lean, in other words, when a lean sensitivity of the downstream oxygen sensor 21 is increased, the constant current circuit 27 outputs the negative constant current (−Ics) so that oxygen is supplied from the atmosphere electrode layer 34 to the exhaust electrode layer 33 through the solid electrolyte layer 32 as shown in FIG. 6A. The supply of oxygen from the atmosphere electrode layer 34 to the exhaust electrode layer 33 promotes oxidation reaction of the rich component (e.g., HC) that exists (remains) around the exhaust electrode layer 33. Hence, the rich component can be removed from around the exhaust electrode layer 33 promptly. Accordingly, the lean component (e.g., NOx) becomes to be easy to react at the exhaust electrode layer 33, and the detection responsiveness of the downstream oxygen sensor 21 can be increased when the actual air-fuel ratio changes to rich to lean. In other words, a lean responsiveness (lean sensitivity) of the downstream oxygen sensor 21 is increased. Here, the lean responsiveness of the downstream oxygen sensor 21 is the detection responsiveness of the downstream oxygen sensor 21 with respect to lean gas that is exhaust gas having an actual air-fuel ratio leaner (i.e., higher) than the stoichiometric air-fuel ratio.

Figure 6B:
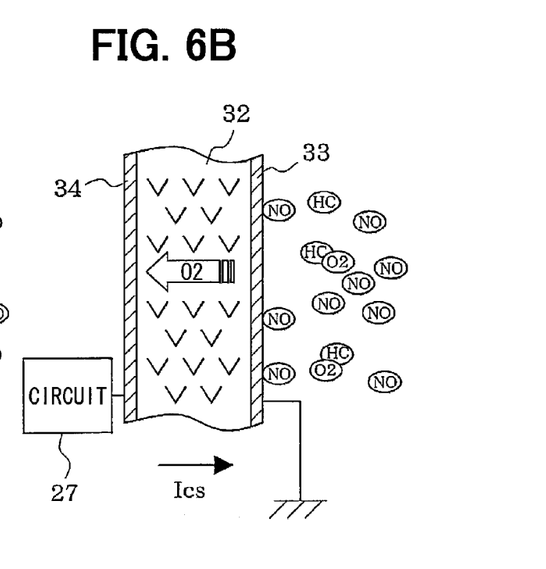
FIG. 6B is a schematic diagram showing a state of components of the exhaust gas around the sensor element when the actual air-fuel ratio changes from lean to rich, and showing a current direction in the sensor element when a rich responsiveness of the sensor element is increased, according to the exemplar embodiment.

When the detection responsiveness of the downstream oxygen sensor 21 is increased in a case where the actual air-fuel ratio changes from lean to rich, in other words, when a rich sensitivity of the downstream oxygen sensor 21 is increased, the constant current circuit 27 outputs the positive constant current (+Ics) so that oxygen is supplied from the exhaust electrode layer 33 to the atmosphere electrode layer 34 through the solid electrolyte layer 32 as shown in FIG. 6B. The supply of oxygen from the exhaust electrode layer 33 to the atmosphere electrode layer 34 promotes reduction reaction of the lean component (e.g., NOx) that exists (remains) around the exhaust electrode layer 33. Hence, the lean component can be removed from around the exhaust electrode layer 33 promptly. Accordingly, the rich component (e.g., HC) becomes to be easy to react at the exhaust electrode layer 33, and the detection responsiveness of the downstream oxygen sensor 21 can be increased when the actual air-fuel ratio changes to lean to rich. In other words, a rich responsiveness (rich sensitivity) of the downstream oxygen sensor 21 is increased. Here, the rich responsiveness of the downstream oxygen sensor 21 is the detection responsiveness of the downstream oxygen sensor 21 with respect to rich gas that is exhaust gas having an actual air-fuel ratio richer (i.e., lower) than the stoichiometric air-fuel ratio.

Figure 7:
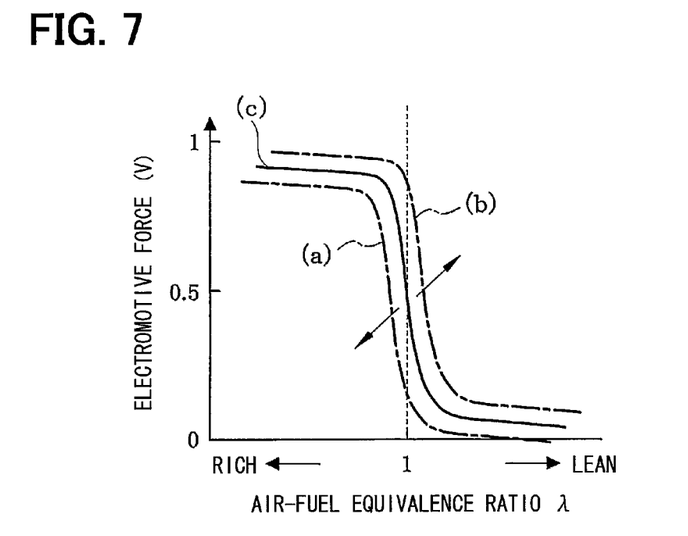
FIG. 7 is a diagram showing a relationship between the air-fuel ratio (air-fuel equivalence ratio $\lambda$) of the exhaust gas and the electromotive force generated by the sensor element according to the exemplar embodiment.
Figure 8:
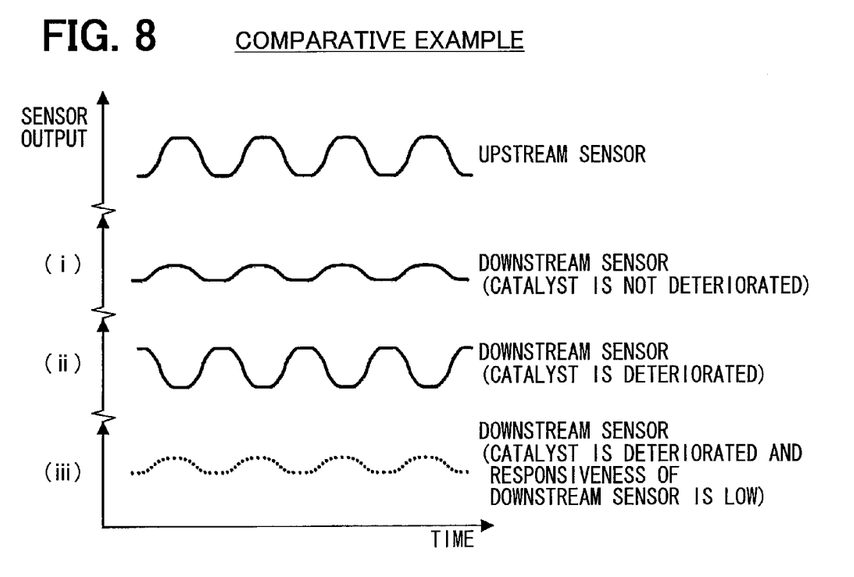
FIG. 8 is a diagram showing an output behavior of an upstream oxygen sensor, and output behaviors of a downstream oxygen sensor (i) when an upstream catalyst is not deteriorated, (ii) when an upstream catalyst is deteriorated, and (iii) when the upstream catalyst is deteriorated in a case where the detection responsiveness of the downstream oxygen sensor is low, in a deterioration diagnosis performed by a deterioration diagnosis device according to a comparative example.

FIG. 7 shows the output characteristic (electromotive force characteristic) of the downstream oxygen sensor 21. The curve (a) shown in FIG. 7 is an output characteristic line of the downstream oxygen sensor 21 when the detection responsiveness (lean sensitivity) is increased in a case where the actual air-fuel ratio changes from rich to lean. The curve (b) shown in FIG. 7 is an output characteristic line of the downstream oxygen sensor 21 when the detection responsiveness (rich sensitivity) is increased in a case where the actual air-fuel ratio changes from lean to rich. The curve (c) shown in FIG. 7 is an output characteristic line same as that shown in FIG. 3, in other words, the curve (c) is when the constant current Ics is not applied to the electrode layers 33 and 34.

As described above, when the detection responsiveness (lean sensitivity) is increased in the case where the actual air-fuel ratio changes from rich to lean, the negative constant current (−Ics) flows between the electrode layers 33 and 34 so that oxygen is supplied from the atmosphere electrode layer 34 to the exhaust electrode layer 33 through the solid electrolyte layer 32 as shown in FIG. 6A. In this case, as shown in FIG. 7, the output characteristic line (a) is located on a richer side of the output characteristic line (c) in air-fuel equivalence ratio λ, and is located on a lower side of the output characteristic line (c) in electromotive force. Thus, even when the actual air-fuel ratio (air-fuel equivalence ratio λ) is within a rich region that is an air-fuel ratio region lower than the stoichiometric air-fuel ratio, the downstream oxygen sensor 21 outputs the lean electromotive force when the actual air-fuel ratio is near the stoichiometric air-fuel ratio. Therefore, with respect to the output characteristic of the downstream oxygen sensor 21, the detection responsiveness (lean sensitivity) of the downstream oxygen sensor 21 can be increased when the actual air-fuel ratio changes from rich to lean.

When the detection responsiveness (rich sensitivity) is increased in the case where the actual air-fuel ratio changes from lean to rich, the positive constant current (+Ics) flows between the electrode layers 33 and 34 so that oxygen is supplied from the exhaust electrode layer 33 to the atmosphere electrode layer 34 through the solid electrolyte layer 32 as shown in FIG. 6B. In this case, as shown in FIG. 7, the output characteristic line (b) is located on a leaner side of the output characteristic line (c) in air-fuel equivalence ratio λ, and is located on a higher side of the output characteristic line (c) in electromotive force. Thus, even when the actual air-fuel ratio (air-fuel equivalence ratio λ) is within a lean region that is an air-fuel ratio region higher than the stoichiometric air-fuel ratio, the downstream oxygen sensor 21 outputs the rich electromotive force when the actual air-fuel ratio is near the stoichiometric air-fuel ratio. Therefore, with respect to the output characteristic of the downstream oxygen sensor 21, the detection responsiveness (rich sensitivity) of the downstream oxygen sensor 21 can be increased when the actual air-fuel ratio changes from lean to rich.

The ECU 25 performs a deterioration diagnosis of the upstream catalyst 18, in which it is determined whether the upstream catalyst 18 is deteriorated or not, when a predetermined diagnosis condition is satisfied. In the deterioration diagnosis, the ECU 25 executes a rich combustion control and a lean combustion control alternately. In the rich combustion control, the air-fuel ratio of the air/fuel mixture supplied to the engine 11 is controlled to become richer. In the lean combustion control, the air-fuel ratio of the air/fuel mixture supplied to the engine 11 is controlled to become leaner. During a predetermined period of the alternately-executed rich and lean combustion controls, the ECU 25 calculates a ratio between an integrated value of output values of the downstream oxygen sensor 21 and an integrated value of output values of the upstream oxygen sensor 20. Subsequently, the ECU 25 compares the integrated value ratio with a predetermined reference value by using the integrated value ratio as a diagnosis parameter. Accordingly, the ECU 25 performs the deterioration diagnosis of the upstream catalyst 18, in other words, for example, the ECU 25 determines whether an oxygen storage capacity of the upstream catalyst 18 is smaller than a predetermined value.

In the present embodiment, when the detection responsiveness of the downstream oxygen sensor 21 decreases, the output characteristic of the downstream oxygen sensor 21 is changed by controlling the constant current circuit 27 so that the deterioration diagnosis of the upstream catalyst 18 is performed accurately, as described later. However, if the output characteristic of the downstream oxygen sensor 21 is not changed by controlling the constant current circuit 27 in the deterioration diagnosis, the deterioration diagnosis may be not performed accurately. In a comparative example shown in FIG. 8, when a detection responsiveness of a downstream oxygen sensor decreases due to time deterioration for example, and when an output characteristic of the downstream oxygen sensor is not changed in a deterioration diagnosis, output behaviors of the downstream oxygen sensor may be similar between when an upstream catalyst is deteriorated and when the upstream catalyst is normal (i.e., not deteriorated) in the deterioration diagnosis as shown by lines (i) and (iii) in FIG. 8. Thus, even when the upstream catalyst is deteriorated, it may be determined that the upstream catalyst is normal (i.e., not deteriorated). Therefore, in the comparative example, a reference value for determining the decrease of the detection responsiveness of the downstream oxygen sensor may be necessarily set tightly, and a life time of the downstream oxygen sensor may thereby become short. In other words, the time to exchange the downstream oxygen sensor due to decrease of its detection responsiveness may become earlier.

Figure 10:
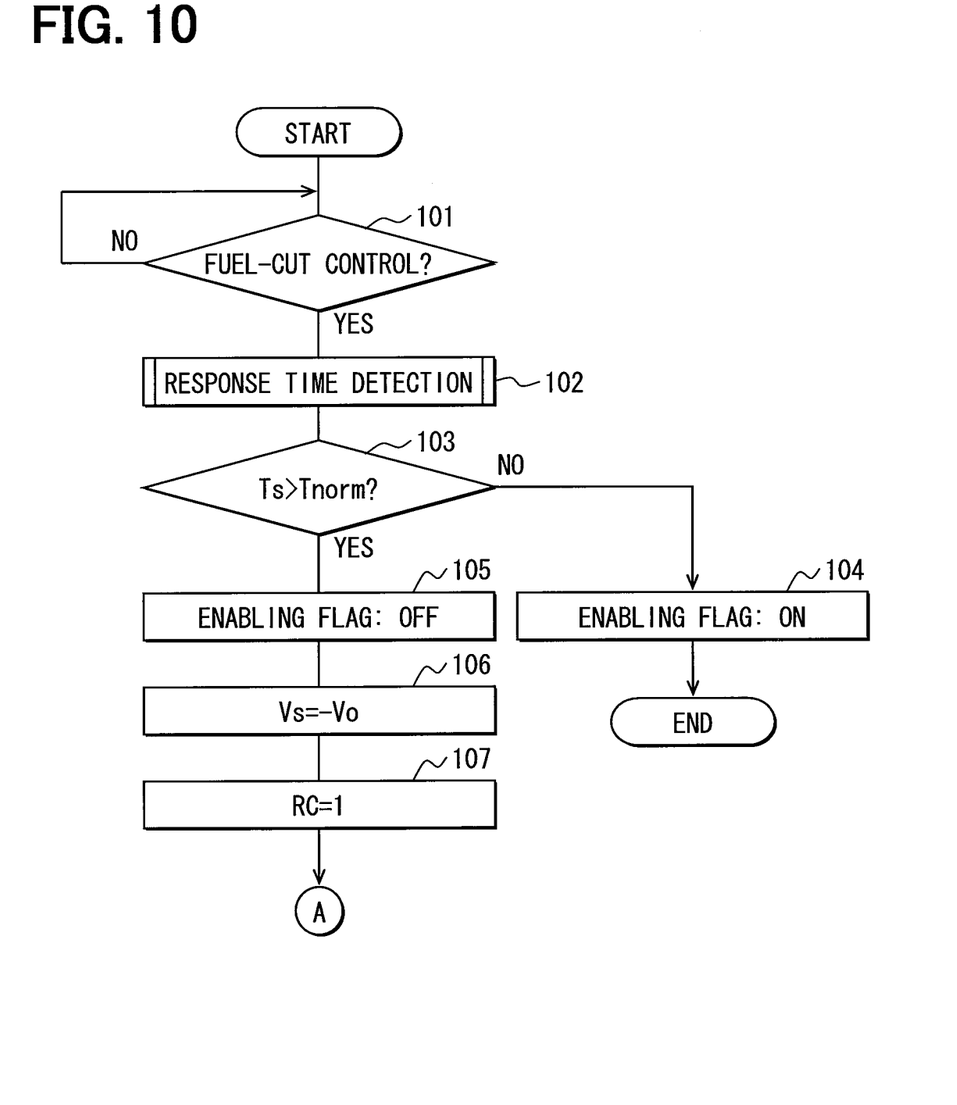
FIG. 10 is a flowchart showing a part of a control process of the response-time correction routine according to the exemplar embodiment.
Figure 11:
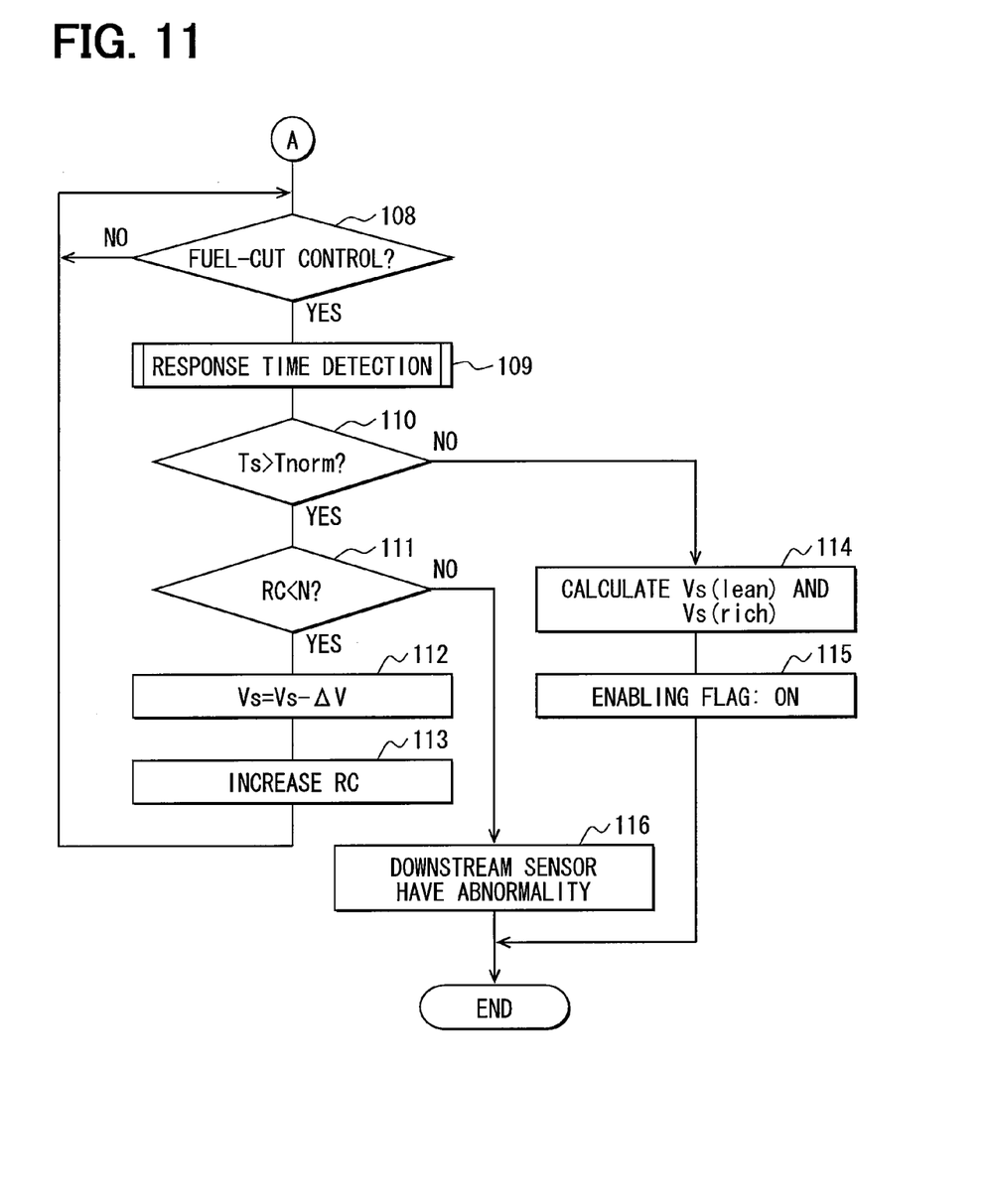
FIG. 11 is a flowchart showing a part of the control process of the response-time correction routine according to the exemplar embodiment.
Figure 12:
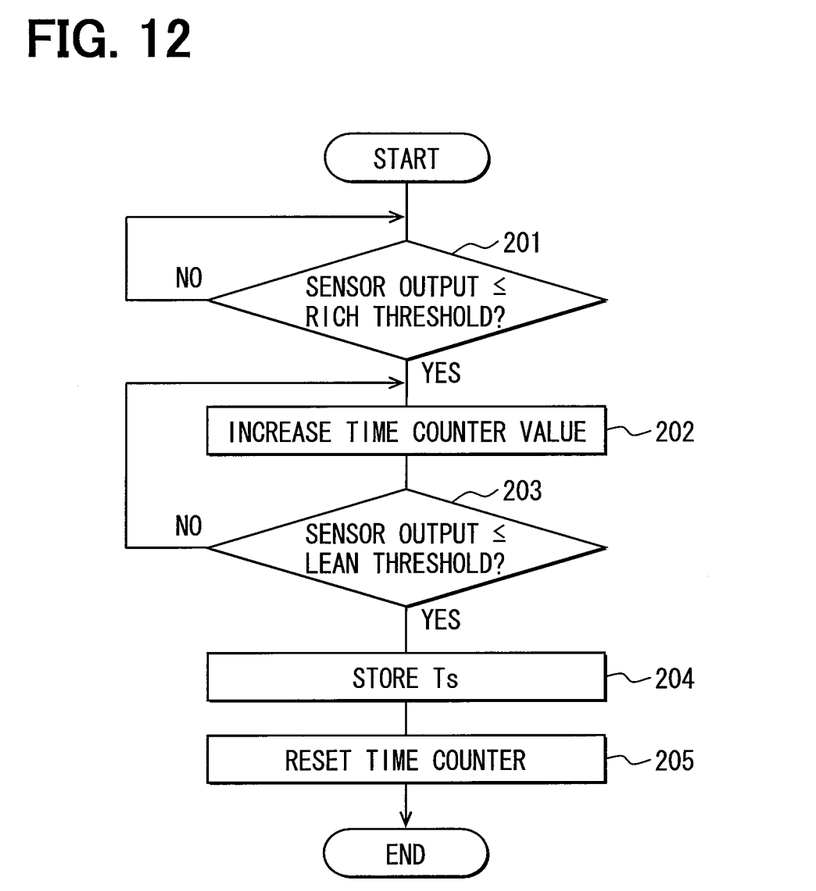
FIG. 12 is a flowchart showing a control process of a response-time detection routine according to the exemplar embodiment.

In order to restrict the above-described phenomenon, in the present embodiment, control routines shown in FIGS. 10 to 12 are performed by the ECU 25 (or the microcomputer 26). Accordingly, the ECU 25 performs a response-time correction control. Specifically, in the response-time correction control, the ECU 25 detects a time (response time Ts) required for the output value of the downstream oxygen sensor 21 to change from a predetermined rich threshold to a predetermined lean threshold in a fuel-cut control in which fuel injection of the engine 11 is stopped. The ECU 25 determines whether the response time Ts is longer than a predetermined reference time Tnorm. When the response time Ts is longer than the reference time Tnorm, the constant current circuit 27 is controlled to apply a voltage to the sensor electrodes of the downstream oxygen sensor 21 such that a constant current flows between the sensor electrodes. By applying the voltage on the sensor electrodes, the output characteristic of the downstream oxygen sensor 21 is changed so that the response time Ts is shorten. Therefore, when the detection responsiveness of the downstream oxygen sensor 21 reduces, the output characteristic of the downstream oxygen sensor 21 can be changed so that its detection responsiveness increases by the response-time correction control.

Figure 9:
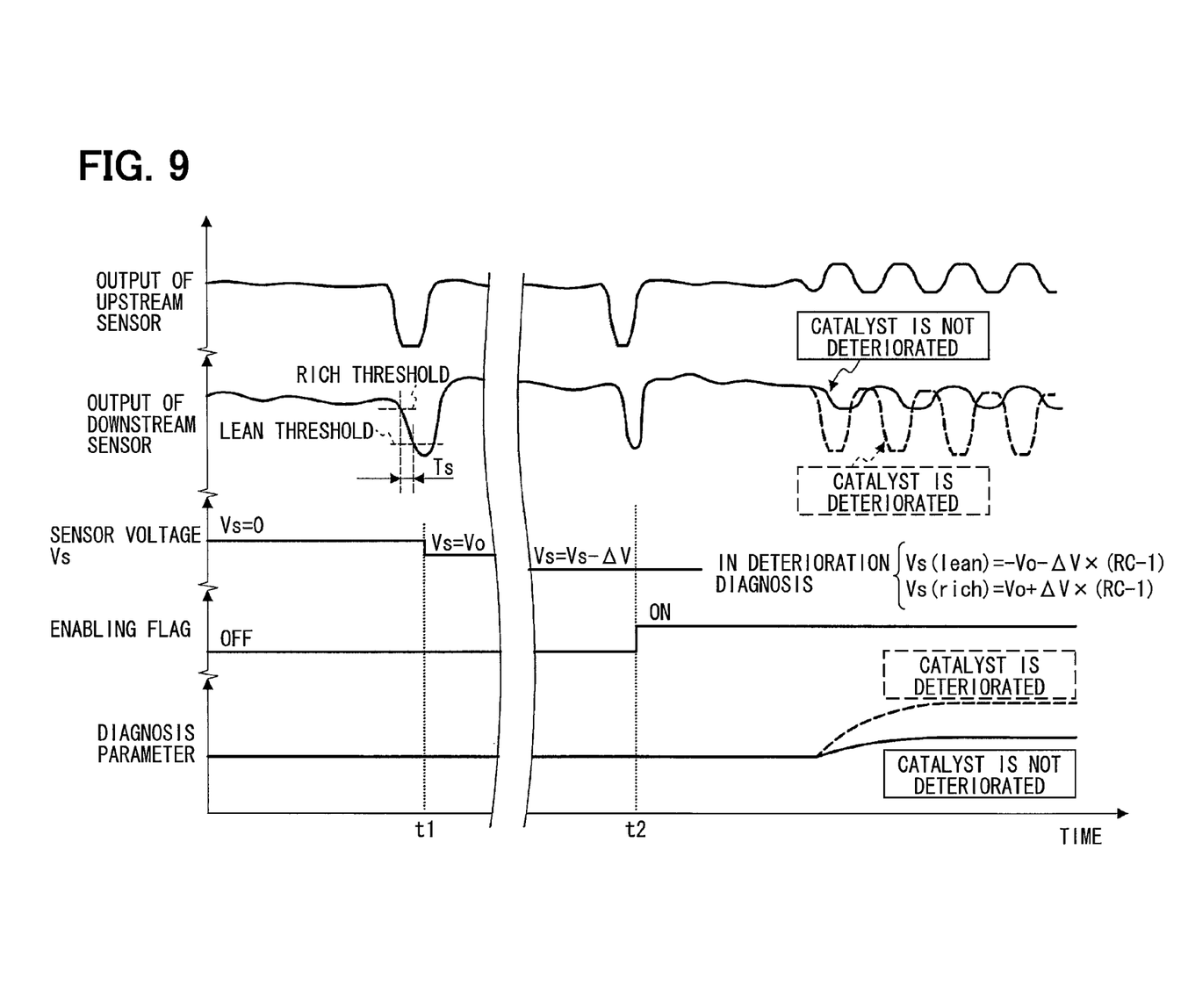
FIG. 9 is a time chart showing changes of an output value of the upstream oxygen sensor, an output value of the downstream oxygen sensor, a sensor voltage, a state of an enabling flag, and a diagnosis parameter, in the deterioration diagnosis device according to the exemplar embodiment.

More specifically, the ECU 25 detects the response time Ts shown in FIG. 9 that is required for the output value of the downstream oxygen sensor 21 to decrease from the rich threshold to the lean threshold during the fuel-cut control. The ECU 25 determines whether the response time Ts is longer than the reference time Tnorm. When the response time Ts is determined to be longer than the reference time Tnorm, the detection responsiveness of the downstream oxygen sensor 21 is determined to be reduced, and an enabling flag is thereby set (kept) OFF at time t1 as shown in FIG. 9 so that the deterioration diagnosis of the upstream catalyst 18 is inhibited.

Additionally, at time t1, a sensor voltage Vs applied on the downstream oxygen sensor 21 (i.e., a voltage applied to the sensor electrodes) is set at an initial value (−V0). By controlling the constant current circuit 27 to apply the sensor voltage Vs between the sensor electrodes, the output characteristic of the downstream oxygen sensor 21 is changed so that the response time Ts is shortened. In other words, when the constant current circuit 27 is controlled to apply the sensor voltage Vs (negative voltage), a negative constant current flows between the sensor electrodes, and the lean responsiveness (lean sensitivity) of the downstream oxygen sensor 21 is increased.

Subsequently, in a next fuel-cut control, the response time Ts is detected newly, and it is determined whether the newly-detected response time Ts is longer than the reference time Tnorm. When the newly-detected response time Ts is longer than the reference time Tnorm, the sensor voltage Vs applied on the downstream oxygen sensor 21 is determined not to reach an appropriate voltage in which the response time Ts can be set equal to or shorter than the reference time Tnorm. Thus, a new sensor voltage Vs is calculated by subtracting a predetermined correction degree ΔV from the lastly-set sensor voltage Vs as shown in the following formula (F1), so that the response time Ts is further shortened.

$$Vs=Vs-\Delta V \quad (F1)$$

The ECU 25 (or the microcomputer 26) performs a process, in which the response time Ts is detected newly in the fuel-cut control, and a process, in which the sensor voltage Vs is changed so that the response time Ts is shortened (i.e., a process in which a new sensor voltage Vs is calculated by subtracting the correction degree ΔV from the lastly-set sensor voltage Vs), repeatedly until the response time Ts becomes equal to or shorter than the reference time Tnorm.

When the response time Ts is determined to be equal to or shorter than the reference time Tnorm, the correction of the detection responsiveness of the downstream oxygen sensor 21 is determined to be finished at time t2. The enabling flag is set ON so that the deterioration diagnosis of the upstream catalyst 18 is enabled to be performed.

A lean sensor voltage Vs(lean) and a rich sensor voltage Vs(rich) used in the deterioration diagnosis of the upstream catalyst 18 are calculated by using a following formulae F2 and F3.

$$Vs(\text{lean})=-V0-\Delta V \times (RC-1) \quad (F2)$$

$$Vs(\text{rich})=V0+\Delta V \times (RC-1) \quad (F3)$$

Here, RC is the number of correction of the sensor voltage Vs (i.e., RC is a count value of a correction counter described later).

The above-described response-time correction control of the present embodiment is performed by the ECU 25 (or microcomputer 26) by executing the control routines shown in FIGS. 10 to 12. These control routines will be described below.

A response-time correction routine shown in FIGS. 10 and 11 is performed repeatedly in a predetermined period during a state in which the ECU 25 is turned ON. A portion of the ECU 25 that performs the response-time correction routine may be used as an example of a response-time correction portion. In the response-time correction routine, it is determined firstly at step 101 whether the fuel-cut control is performed. When the fuel-cut control is determined to be performed, a control operation of step 102 is performed. At step 102, a response-time detection routine shown in FIG. 12 is performed so that the response time Ts (i.e., a time required for the output value of the downstream oxygen sensor 21 to decrease from the rich threshold to the lean threshold) is detected. A portion of the ECU 25 (or the microcomputer 26) that performs the response-time detection routine may be used as an example of a response-time detection portion.

At next step 103, it is determined whether the response time Ts is longer than the reference time Tnorm. When the response time Ts is determined to be equal to or shorter than the reference time Tnorm, the detection responsiveness of the downstream oxygen sensor 21 is determined to be ensured. Thus, the sensor voltage Vs of the downstream oxygen sensor 21 is kept at a normal value (e.g., 0), and a control operation of step 104 is performed. At step 104, the enabling flag is set ON, so that the deterioration diagnosis of the upstream catalyst 18 is enabled to be performed.

On the other hand, when the response time Ts is determined to be longer than the reference time Tnorm at step 103, the detection responsiveness of the downstream oxygen sensor 21 is determined to be low. Thus, at next step 105, the enabling flag is kept (or set) OFF, so that the deterioration diagnosis of the upstream catalyst 18 is inhibited.

At next step 106, the sensor voltage Vs of the downstream oxygen sensor 21 is set at the initial value (−V0) as a following formula F4.

$$Vs=V0 \quad (F4)$$

Accordingly, the constant current circuit 27 is controlled to apply the sensor voltage Vs (Vs=V0) to the sensor electrodes of the downstream oxygen sensor 21 so that a constant current flows between the sensor electrodes. As a result, the output characteristic of the downstream oxygen sensor 21 is changed so that the response time Ts is shortened. At next step 107, the count value RC of the correction counter is set at 1. The correction counter counts the number of correction of the sensor voltage Vs.

Subsequently, a control operation of step 108 shown in FIG. 11 is performed. At step 108, it is determined whether the fuel-cut control is performed. When the fuel-cut control is determined to be performed at step 108, the response-time detection routine shown in FIG. 12 is performed at step 109 so that the response time Ts is detected.

At next step 110, it is determined whether the response time Ts detected at step 109 is longer than the reference time Tnorm. When the response time Ts is determined to be longer than the reference time Tnorm, the sensor voltage Vs is determined not to reach the appropriate voltage, and a control operation of step 111 is performed. At step 111, it is determined whether the count value RC of the correction counter is lower than a predetermined number N.

When the count value RC of the correction counter is determined to be lower than the predetermined number N at step 111, a control operation of step 112 is performed. At step 112, a new sensor voltage Vs is calculated by subtracting the predetermined correction degree ΔV from the lastly-set sensor voltage Vs as described in a following formula F5 so that the response time Ts is further shortened.

$$Vs=Vs-\Delta V \quad (F5)$$

Accordingly, the constant current circuit 27 is controlled to apply the new sensor voltage Vs (Vs=Vs−ΔV) to the sensor electrodes of the downstream oxygen sensor 21 so that a constant current flows between the sensor electrodes. As a result, the output characteristic of the downstream oxygen sensor 21 is changed so that the response time Ts is shortened.

Subsequently, at step 113, the count value RC of the correction counter is increased by 1, and the control operation of step 108 is performed. As described above, in the response-time correction control, the ECU 25 (or the microcomputer 26) performs the process, in which the response time Ts is detected during the fuel-cut control, and the process, in which the sensor voltage Vs is changed so that the response time Ts is shortened (i.e., the process in which a new sensor voltage Vs is calculated by subtracting the correction degree ΔV from the lastly-set sensor voltage Vs), repeatedly until the response time Ts becomes equal to or shorter than the reference time Tnorm.

When the response time Ts detected at step 109 is determined to be equal to or shorter than the reference time Tnorm at step 110, the correction of the detection responsiveness of the downstream oxygen sensor 21 is determined to be finished, and a control operation of step 114 is performed. At step 114, the lean sensor voltage Vs(lean) and the rich sensor voltage Vs(rich) used in the deterioration diagnosis are calculated by using a following formulae F6 and F7.

$$Vs(\text{lean}) = -V0 - \Delta V \times (RC-1) \tag{F6}$$

$$Vs(\text{rich}) = V0 + \Delta V \times (RC-1) \tag{F7}$$

At next step 115, the enabling flag is set ON, so that the deterioration diagnosis of the upstream catalyst 18 is enabled to be performed. When the execution condition of the deterioration diagnosis is satisfied, the deterioration diagnosis of the upstream catalyst 18 is performed. In the deterioration diagnosis, when the rich combustion control and the lean combustion control are performed alternately, the sensor voltage Vs of the downstream oxygen sensor 21 is alternately switched between the rich sensor voltage Vs(rich) and the lean sensor voltage Vs(lean).

When the count value RC of the correction counter is determined to be equal to or higher than the predetermined number N at step 111, the downstream oxygen sensor 21 is determined to have an abnormality at step 116. In other words, the downstream oxygen sensor 21 is determined to have an abnormality when the response time Ts does not become equal to or shorter than the reference time Tnorm (i.e., the deterioration diagnosis of the upstream catalyst 18 is inhibited) even though the sensor voltage Vs is changed the predetermined number N times so that the response time Ts is shortened.

Portions of the ECU 25 (or the microcomputer 26) that perform the control operations of steps 103, 104, 105, 110, 115 may be used as examples of a diagnosis control portion. The diagnosis control portion inhibits the deterioration diagnosis of the upstream catalyst 18 when the response time Ts is longer than the reference time Tnorm, and enables the deterioration diagnosis to be performed when the response time Ts is equal to or shorter than the reference time Tnorm. Portions of the EUC 25 (or the microcomputer 26) that perform the control operations of steps 111, 116 may be used as examples of an abnormality determination portion. The abnormality determination portion determines that the downstream exhaust-gas sensor has an abnormality when the response time Ts is still longer than the reference time Tnorm even in a case where the change of the voltage Vs is performed by the response-time correction portion predetermined number times. Portions of the ECU 25 (or the microcomputer 26) that perform the control operations of steps 103, 106, 110, 112 may be used as examples of the response-time correction portion. The response-time correction portion changes the output characteristic of the downstream exhaust-gas sensor by controlling the constant current supply portion and applying a constant current and a voltage to the pair of electrodes so as to shorten the response time Ts when the response time Ts detected by the response-time detection portion is longer than a predetermined reference time Tnorm.

The response-time detection routine shown in FIG. 12 is a subroutine performed at steps 102 and 109 of the response-time correction routine shown in FIGS. 10 and 11. In the response-time detection routine, it is determined firstly at step 201 whether the output value (sensor output) of the downstream oxygen sensor 21 is equal to or lower than the predetermined rich threshold (e.g., 0.7 V) after a start of the fuel-cut control. When the output value of the downstream oxygen sensor 21 is determined to be equal to or lower than the rich threshold at step 201, a count value of a time counter that measures the response time Ts is increased at step 202.

At next step 203, it is determined whether the output value of the downstream oxygen sensor 21 is equal to or lower than the predetermined lean threshold (e.g., 0.1 V) after the start of the fuel-cut control. When the output value of the downstream oxygen sensor 21 is determined to be higher than the lean threshold at step 203, the control operation of step 202 is performed again so that the count value of the time counter is increased.

When the output value of the downstream oxygen sensor 21 is determined to be equal to or lower than the lean threshold at step 203, a control operation of step 204 is performed. At step 204, the count value of the time counter (i.e., a time required for the output value of the downstream oxygen sensor 21 to decrease from the rich threshold to the lean threshold) is stored as the response time Ts. Subsequently, at step 205, the count value of the time counter is reset at 0. Portions of the ECU 25 (or the microcomputer 26) that perform the control operations of steps 201 to 205 may be used as examples of the response-time detection portion. The response-time detection portion detects a response time Ts required for the output value of the downstream exhaust-gas sensor to change from a predetermined rich threshold to a predetermined lean threshold during the fuel-cut control in which fuel injection of the engine is stopped, before the deterioration diagnosis.

In the above-describe present embodiment, a constant current flows between the sensor electrodes of the downstream oxygen sensor 21 by using the constant current circuit 27 provided outside the downstream oxygen sensor 21. Thus, the output characteristic of the downstream oxygen sensor 21 can be changed so that the lean responsiveness and the rich responsiveness can be increased. Moreover, there is no need to incorporate an auxiliary electrochemical cell or the like to an inside of the downstream oxygen sensor 21. Therefore, the output characteristic of the downstream oxygen sensor 21 can be changed without great design changes and cost increase.

When the response time Ts detected during the fuel-cut control of the engine 11 is determined to be longer than the reference time Tnorm, the constant current circuit 27 is controlled to apply the sensor voltage Vs to the sensor electrodes of the downstream oxygen sensor 21 so that a constant current flows between the sensor electrodes. Accordingly, the output characteristic of the downstream oxygen sensor 21 is changed so that the response time Ts is shortened. Therefore, in the present embodiment, when the detection responsiveness of the downstream oxygen sensor 21 is low, the output characteristic of the downstream oxygen sensor 21 can be changed such that the detection responsiveness of the downstream oxygen sensor 21 is increased. As a result, it can be avoided that the output behavior of the downstream oxygen sensor 21 becomes similar between when the upstream catalyst 18 is not deteriorated and when the upstream catalyst 18 is deteriorated. As shown in FIG. 9, a difference of the diagnosis parameter between when the upstream catalyst 18 is not deteriorated and when the upstream catalyst 18 is deteriorated can be enlarged. Therefore, when the upstream catalyst 18 is deteriorated, it can be restricted that the upstream catalyst 18 is determined not to be deteriorated, i.e., it can be restricted that the upstream catalyst 18 is determined to be normal. In other words, the upstream catalyst 18 can be determined to be deteriorated accurately when the upstream catalyst 18 is deteriorated. Consequently, decrease of an accuracy of the deterioration diagnosis of the upstream catalyst 18 due to the decrease of the detection responsiveness of the downstream oxygen sensor 21 can be restricted. The accuracy of the deterioration diagnosis of the upstream catalyst 18 can be increased. Furthermore, there can be no need to set so tightly the reference value that is for determining the decrease of the detection responsiveness of the downstream oxygen sensor 21, and the life time of the downstream oxygen sensor 21 can be thereby lengthened. In other words, the time to exchange the downstream oxygen sensor 21 due to decrease of its detection responsiveness can be retarded.

In the present embodiment, when the response time Ts is determined to be longer than the reference time Tnorm, and when the sensor voltage Vs is applied to the sensor electrodes of the downstream oxygen sensor 21, the response time Ts is detected newly during a next fuel-cut control. Additionally, when the newly-detected response time Ts is determined to be longer than the reference time Tnorm, the sensor voltage Vs is changed so that the response time Ts is further shortened. Therefore, even when the sensor voltage Vs set firstly after a start of the engine 11 does not reach the appropriate voltage in which the response time Ts can be made to be equal to or shorter than the reference time Tnorm, the sensor voltage Vs can be corrected so that the sensor voltage Vs reaches the appropriate voltage.

In the present embodiment, the process, in which the response time Ts is detected newly in the fuel-cut control, and the process, in which the sensor voltage Vs is changed so that the response time Ts is shortened, are performed repeatedly until the response time Ts becomes equal to or shorter than the reference time Tnorm. Therefore, the correction of the sensor voltage Vs can be performed repeatedly until the sensor voltage Vs reaches the appropriate voltage.

In the above-described embodiment, the present disclosure is applied to the emission control system 1 that performs the deterioration diagnosis in which it is determined whether the upstream catalyst 18 is deteriorated. In the deterioration diagnosis, specifically, the ECU 25 (or the microcomputer 26) calculates the ratio as the diagnosis parameter between an integrated value of output values of the downstream oxygen sensor 21 and an integrated value of output values of the upstream oxygen sensor 20 during the predetermined period of the alternately-executed rich and lean combustion controls. Subsequently, the ECU 25 (or the microcomputer 26) compares the integrated value ratio (diagnosis parameter) with a predetermined reference value to determine whether the upstream catalyst 18 is deteriorated. However, a method of the deterioration diagnosis is not limited to the above-described method, and may be changed variably. The present disclosure may be applied at least to a system that performs a deterioration diagnosis by using a downstream exhaust sensor provided downstream of a catalyst in a flow direction of exhaust gas.

In the above-described embodiment, the constant current circuit 27 is connected to the atmosphere electrode layer 34 of the downstream oxygen sensor 21 (sensor element 31). However, for example, the constant current circuit 27 may be connected to the exhaust electrode layer 33 of the downstream oxygen sensor 21 (sensor element 31), or the constant current circuit 27 may be connected to both the atmosphere electrode layer 34 and the exhaust electrode layer 33.

In the above-described embodiment, the present disclosure is applied to the emission control system 1 including the downstream oxygen sensor 21 that has the cup-like shaped sensor element 31. However, for example, the present disclosure may be applied to an emission control system including an oxygen sensor that has a sensor element having a laminated structure.

In the above-described embodiment, the present disclosure is applied to the emission control system 1 in which the downstream oxygen sensor 21 is located downstream of the upstream catalyst 18 in the flow direction of the exhaust gas. However, the present disclosure is not limited to the upstream catalyst 18 or the downstream oxygen sensor 21. The present disclosure may be applied to an emission control system in which an exhaust gas sensor, such as an oxygen sensor or an air-fuel ratio sensor, is located downstream of a catalyst for purification of exhaust gas in a flow direction of the exhaust gas.

Additional advantages and modifications will readily occur to those skilled in the art. The disclosure in its broader terms is therefore not limited to the specific details, representative apparatus, and illustrative examples shown and described.

What is claimed is:

1. A deterioration diagnosis device which performs a deterioration diagnosis of a catalyst used for purification of exhaust gas discharged from an internal combustion engine, the deterioration diagnosis device comprising:
   a downstream exhaust-gas sensor provided downstream of the catalyst in a flow direction of the exhaust gas to detect and output an air-fuel ratio of the exhaust gas or to detect and output whether the exhaust gas is rich or lean such that an output value of the downstream exhaust-gas sensor is used in at least in the deterioration diagnosis, the downstream exhaust-gas sensor including a sensor element that includes a pair of electrodes and a solid electrolyte body located between the pair of electrodes;
   a constant current supply portion which applies a constant current and a voltage to the pair of electrodes to change an output characteristic of the downstream exhaust-gas sensor; and
   a controller configured to;
      detect a response time required for the output value of the downstream exhaust-gas sensor to change from a predetermined rich threshold to a predetermined lean threshold during a fuel-cut control in which fuel injection of the engine is stopped; and
      change the output characteristic of the downstream exhaust-gas sensor by controlling the constant current supply portion and applying the constant current and the voltage to the pair of electrodes so as to shorten the response time when the response time detected by the controller is longer than a predetermined reference time.

2. The deterioration diagnosis device according to claim 1, wherein the controller is configured to inhibit the deterioration diagnosis of the catalyst when the response time is longer than the reference time, and enables the deterioration diagnosis to be performed when the response time is equal to or shorter than the reference time.

3. The deterioration diagnosis device according to claim 1, wherein
   the controller is configured to detect the response time newly during a next fuel-cut control when the controller changes the output characteristic of the downstream exhaust-gas sensor, and
   the controller is configured to change the voltage applied to the pair of electrodes so as to further shorten the response time when the newly-detected response time is longer than the reference time.

4. The deterioration diagnosis device according to claim 3, wherein the detection of the response time during the fuel-cut control, and the change of the voltage to further shorten the response time are performed repeatedly until the response time becomes equal to or shorter than the reference time.

5. The deterioration diagnosis device according to claim 4, wherein the controller is configured to determine that the downstream exhaust-gas sensor has an abnormality when the response time is longer than the reference time in a case where predetermined number changes of the voltage is performed.

6. The deterioration diagnosis device according to claim 1, wherein the constant current supply portion includes a constant current circuit connected to the pair of electrodes to supply the constant current and the voltage to the pair of electrodes.

7. The deterioration diagnosis device according to claim 1, wherein the response time is responsiveness of the downstream exhaust-gas sensor to at least one of a lean downstream exhaust gas and a rich downstream exhaust gas.

8. The deterioration diagnosis device according to claim 1, wherein changing the voltage changes the downstream exhaust-gas sensor between a rich sensor voltage and a lean sensor voltage.

9. The deterioration diagnosis device according to claim 1, wherein when the constant current and the voltage are applied to the pair of electrodes, a reduction reaction of a lean component of the exhaust gas or an oxidation reaction of a rich component of the exhaust gas can be accelerated around the pair of electrodes based upon a value of the voltage.

* * * * *